United States Patent [19]

Lavoie et al.

[11] Patent Number: 5,525,662
[45] Date of Patent: Jun. 11, 1996

[54] FUNCTIONALIZATION OF POLYMERS VIA ENAMINE OF ACETOACETATE

[75] Inventors: Alvin C. Lavoie, Lansdale; Daniel A. Bors, Maple Glen; Ward T. Brown, North Wales, all of Pa.

[73] Assignee: Rohm and Haas Company, Philadelphia, Pa.

[21] Appl. No.: 91,489

[22] Filed: Jul. 14, 1993

[51] Int. Cl.$^6$ ............................................. C08F 8/32
[52] U.S. Cl. .................. 524/558; 525/102; 525/293; 525/328.6; 525/379; 525/382
[58] Field of Search ........................ 525/382, 102, 525/379, 293; 524/558

[56] References Cited

U.S. PATENT DOCUMENTS

| | | |
|---|---|---|
| 3,328,325 | 6/1967 | Zdanowski . |
| 3,467,610 | 9/1969 | Fiarman et al. . |
| 4,150,005 | 4/1979 | Gehman et al. . |
| 4,626,567 | 12/1986 | Chang . |
| 4,908,403 | 3/1990 | Spada et al. . |
| 4,960,924 | 10/1990 | Bors et al. . |
| 4,987,186 | 1/1991 | Akiyama et al. . |
| 4,988,762 | 1/1991 | Overbeek et al. . |
| 5,017,676 | 5/1991 | Cuscurida . |
| 5,055,506 | 10/1991 | Knutson . |
| 5,124,384 | 6/1992 | Goldstein . |
| 5,362,816 | 11/1994 | Snyder et al. ............... 525/329.9 |

FOREIGN PATENT DOCUMENTS

| | | |
|---|---|---|
| 358358 | 3/1990 | European Pat. Off. . |
| 442653 | 8/1991 | European Pat. Off. . |
| 483915 | 10/1991 | European Pat. Off. . |
| 483583 | 5/1992 | European Pat. Off. . |
| 390370 | 6/1993 | European Pat. Off. . |
| 555774 | 8/1993 | European Pat. Off. . |
| 573142 | 12/1993 | European Pat. Off. . |
| 4189874 | 7/1992 | Japan . |
| 9316133 | 8/1993 | WIPO . |

OTHER PUBLICATIONS

"Reactive Methacrylate Polymer Granulates", Ishidoya, Masahiro, et al., Chemical Abstracts, vol. 114, No. 26, p. 51, No. 248 511D (1991).

"Reaction Behaviour of Monomeric β–Ketoesters 2. Synthesis, Characterization and Polymerization of Methacrylate Group Containing Enamines", Norbert Moszner, et al., Polymer Bulletin, vol. 32, pp. 419–426 (1994).

"Fast Curing Aqueous Adhesives", Shimokawa, Wataru, Chemical Abstracts, vol. 105, No. 10, p. 59, No. 80 186Q (1986).

"Applications for The Acetoacetyl Functionality in Thermoset Coatings", Del Rector, F. et al., Chemical Abstracts, vol. 109, No. 12, p. 80, No. 94771W (1988).

"Comparison of Methods for The Preparation of Acetoacetylated Coating Resins", J. S. Witzeman; W. Dell Nottingham, F. J. Del Rector, Journal of Coatings Technology, vol. 62, 1990, 101.

"Feasibility of Using Alkoxy Silane Functional Monomers for The Development of Crosslinking Emulsions", T. R. Bourne, B. G. Bufkin, G. C. Wildman and J. R. Grave, Journal of Coatings Technology, vol. 54, No. 684, Jan. 1982.

Primary Examiner—Bernard Lipman
Attorney, Agent, or Firm—David T. Banchik

[57] ABSTRACT

The present invention relates to the preparation of polymers bearing reactive functional groups. More particularly, this invention relates to the preparation of polymers containing functional acetoacetate groups and then following the polymerization reacting the acetoacetate group with a functional amine to form an enamine.

Polymers of the present invention have many uses including coatings, sealants, adhesives and saturant applications, and are most useful as solutions or dispersions in water or water-cosolvent mixtures.

5 Claims, No Drawings

1

FUNCTIONALIZATION OF POLYMERS VIA ENAMINE OF ACETOACETATE

FIELD OF THE INVENTION

The present invention relates to the preparation of polymers bearing reactive functional groups. More particularly, this invention relates to the preparation of polymers containing functional acetoacetate groups and then following the polymerization reacting the acetoacetate group with a functional amine to form an enamine.

Polymers of the present invention have many uses including coatings, sealants, adhesives and saturant applications, and are most useful as solutions or dispersions in water or water-cosolvent mixtures.

Coatings produced from polymers of the present invention exhibit improved properties such as, for example, solvent resistance, dirt pickup resistance, print and block resistance, mar resistance, adhesion and tensile properties, such as impact resistance and tensile strength.

BACKGROUND OF THE INVENTION

It is generally known to be useful to modify the properties of polymers by incorporating desired functional groups of one sort or another into the polymer molecules. The desired functional groups may be incorporated either by employing, as a monomer during the preparation of the polymer, a compound which already has such functional groups, or by post-reacting the polymer having precursor groups with suitable reagents to convert to the desired functional groups.

A novel, unanticipated and useful process is now discovered for post-reacting a polymer having precursor groups for purpose of incorporating desired functional groups into a polymer.

An advantage of the invention is to provide a process which produces a functional polymer by post-polymerization reaction.

Another advantage of the invention is to provide new monomers bearing functional groups.

An additional advantage of the invention is to provide polymers bearing functional groups which are incompatible with polymerization processes.

PRIOR RELATED ART

Although it is generally known to modify the properties of polymers by incorporating desired functional groups, none of the related art discloses the preparation of polymers containing functional acetoacetate groups, and postpolymerization reacts the acetoacetate group with a functional amine to form an enamine.

European Patent Application EP 0 442 653 A2 discloses a process for the production of a polymer having desired groups, denoted as Y, by reacting a polymer having carbon or nitrogen-bound-$NH_2$ and/or —$NH_2$— precursor groups, which groups are reactable with enolic carboxyl groups, with at least one compound having a single enolic carboxyl group and at least one Y, wherein by an enolic carbonyl group is meant a carboxyl group having enolic character by virtue of being bonded to an alpha methylene or methane group which is itself bonded to an electron withdrawing group.

European Patent Application EP 0 483 583 A2 discloses that polyacetoacetates or polyacetoacetamides can be reacted with amino group-containing alkoxy-silanes to give polyenamines which permit a long processing time and which crosslink without the action of atmospheric humidity. This is alleged to be an advantage for film thickness greater than $50_\mu$.

SUMMARY OF THE INVENTION

In one aspect of the invention, an acetoacetate functional polymer is reacted with a compound bearing an amine group and at least one additional functional group, to produce a polymer bearing the additional functional group attached through the enamine of the acetoacetate group.

In another aspect of the invention, acetoacetate functional monomer is reacted with a compound bearing an amine group and at least one additional functional group, to produce a new functional monomer. This monomer can be subsequently polymerized to form a functionalized polymer.

DETAILED DESCRIPTION

In one aspect of the invention, an acetoacetate functional polymer is reacted with a compound bearing an amine group and at least one additional functional group, to produce a polymer bearing the additional functional group attached through the enamine of the acetoacetate group.

In another aspect of the invention, acetoacetate functional monomer is reacted with a compound bearing an amine group and at least one additional functional group, to produce a new functional monomer. This monomer can be subsequently polymerized to form a functionalized polymer.

In still another aspect of the invention, polymers prepared by polymerizing acetoacetate functional monomers are reacted with a compound bearing an amine functional group and at least one incompatible functional group, a group which would not have maintained functional viability under the conditions of the polymerization process. A new polymer is produced, bearing the incompatible functional group attached to the polymer via the enamine of the acetoacetate group.

In a further aspect of the invention, a polymer functionalization package and a method of functionalizing is provided. Acetoacetate functional polymer backbones can be prepared, and the proportion of compound bearing an amine group and at least one additional functional group can be varied over a range from about a molar excess of amine, based on acetoacetate, to substantially less than a molar excess, to fit the particular property requirements of the end use application. This allows one to maintain an inventory of relatively few types of polymerization products and offer a diverse line of end use polymers by custom-functionalizing the polymers with the selected amount of amine functional reactant.

In still a further aspect of the invention, a method is provided which allows the incorporation of desired functional groups, concentrated in desired areas, for example, at the surface of a polymer particle.

Polymers bearing functional groups attached through the enamine of acetoacetate groups are useful in coatings, adhesives, polymer blends, plastics additives, dispersants, flocculants and separation technologies.

Polymers

The preferred polymers for use in this invention are vinyl polymers with pendant acetoacetate groups, alternately known as beta-ketoesters. The term "pendant" is used in the specification to mean "attached to the polymer backbone and available for further reaction." Pendant should not be read in the strict sense which would exclude the attachment of such groups at the termini of a polymer chain. Thus, polymer having acetoacetate functionality introduced on the chain end by an acetoacetate functional mercaptan, as taught in U.S. Patent 4,960,924, would be useful in this invention. Generally, the pendant acetoacetate groups are attached to the polymer backbone via an organic divalent radical $R^1$ which in turn is attached to the acetoacetate moiety or by a trivalent organic radical $R^2$ bearing two acetoacetate groups.

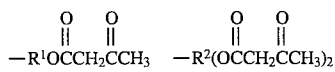

The acetoacetate functional polymers can be prepared by means known in the art. A preferred method is polymerization through incorporation which includes an acetoacetate functional monomer. A preferred monomer is acetoacetoxyethyl methacrylate which is conveniently referred to throughout this specification as AAEM, shown below.

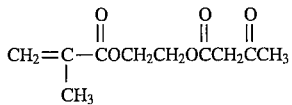

Examples of other monomers useful for introduction of acetoacetate functionality are acetoacetoxyethyl acrylate, acetoacetoxypropyl methacrylate, allyl acetoacetate, acetoacetoxybutyl methacrylate, 2,3-di(acetoacetoxy)propyl methacrylate, and the like. In general, any polymerizable hydroxy functional monomer can be converted to the corresponding acetoacetate by reaction with diketene or other suitable acetoacetylating agent (See e.g. *Comparison of Methods for the Preparation of Acetoacetylated Coating Resins*, Witzeman, J. S.; Dell Nottingham, W.; Del Rector, F. J. Coatings Technology; Vol. 62, 1990, 101. (and references contained therein)).

The vinyl polymers of this invention are most often copolymers of the acetoacetate functional monomer and other monomers. Examples of useful comonomers are simple olefins such as ethylene, alkyl acrylates and methacrylates where the alkyl group has 1 to 20 carbon atoms (more preferably 1 to 8 carbon atoms), vinyl acetate, acrylic acid, methacrylic acid, acrylonitrile, styrene, isobornyl methacrylate, acrylamide, hydroxyethyl acrylate and methacrylate, hydroxypropyl methacrylate and acrylate, N-vinyl pyrolidinone, butadiene, isoprene, vinyl halides such as vinyl chloride and vinylidene chloride, alkyl maleates, alkyl fumarates, fumaric acid, maleic acid, itaconic acid, and the like. It is also possible and sometimes desirable to include low levels of divinyl or polyvinyl monomers such as glycol polyacrylates, allyl methacrylate, divinyl benzene, and the like, to introduce a controlled amount of gel in the latex particle. It is important, however, to be sure that when this is done, the quality of the film formation is not seriously impaired. Additionally, one may wish to include chain transfer agents to control molecular weight of the polymer.

The acetoacetate functional polymer may contain from about 0.5% to 100% of the acetoacetate functional monomer by weight. In any application, the amount of acetoacetate functional monomer required will vary from case to case depending upon the desired degree of post functionalization necessary for the particular end-use application. Generally, however, the acetoacetate monomer concentration will be between 1 and 40%. Conventional coatings will usually contain from about 0.5 to 20% acetoacetate monomer by weight. Polymers having a molecular weight of from 1,000 to over one million can be used. The lower molecular weight polymers should contain a sufficiently high level of acetoacetate to maximize the degree of post functionalization. For example, a copolymer of AAEM having a molecular weight under 10,000 would typically contain 30% or more of AAEM.

Generally, the vinyl polymer is prepared as a dispersion or emulsion polymer in water by a suitable free radical initiated polymerization technique, using a free radical initiator and appropriate heating. Since a film-forming polymer is sometimes desired, useful emulsion polymers will generally have glass transition temperatures under 60° C., since these polymers with coalescent will form good quality films at ambient temperatures. If soluble polymers are used in the film formation process, polymers of higher glass transition temperature are readily used since they are film-forming.

In certain aspects of the invention, polymerization in an aqueous medium and, in particular, aqueous emulsion polymerization, is used to prepare the polymer. Conventional dispersants can be used (e.g. anionic and/or nonionic emulsifiers such as alkali or ammonium alkyl sulfates, alkyl sulfonic acids, and fatty acids, oxyethylated alkyl phenols, and the like). The amount of dispersant used is usually 0.1 to 6% by weight based on the weight of total monomer. Either thermal or redox initiation processes may be used. Conventional free radical initiators may be used (hydrogen peroxide, organic hydroperoxides such as t-butyl hydroperoxide, cumene hydroperoxide, t-amyl hydroperoxide, ammonium and/or alkali persulfates, organic peroxides such as t-butyl perpivalate, t-butyl perbenzoate, benzoyl peroxide, di(n-propyl) peroxydicarbonate, acetyl cyclo-hexylsulfonyl peroxide, and the like); typically 0.05 to 3.0 % by weight based on the weight of total monomer. Redox systems using the same initiators coupled with a suitable reductant (for example: reducing sugars such as isoascorbic acid, sodium bisulfite, sodium thiosulfate, hydroxyl amine, hydrazine, sodium hydrosulfite) can be used at similar levels, oftentimes in conjunction with a metal catalyst such as salts of transition metals, examples of which are iron sulfate, copper sulfate, vanadium sulfate, and the like. Additionally, non-oxidizing thermal initiators such as 2,2'-Azo-bis-isobutyronitrile, 4,4'-Azo-bis(4-cyanopentanoic acid), 2,2'-Azo-bis(2-amidinopropane) dihydrochloride, and the like. Frequently, a low level of chain transfer agent such as a mercaptan (for example: n-octyl mercaptan, n-dodecyl mercaptan, butyl or methyl mercaptopropionate, mercaptopropionic acid at 0.05 to 6% by weight based on total weight of monomer) is employed to control molecular weight.

The invention may also be practiced using a solvent-soluble or water-soluble polymer. When this is desired, the polymer may be prepared directly in water if the monomer mix is water-soluble or, as is most often the case, the polymerization solvent is a water miscible solvent such as isopropanol, butyl cellosolve, propylene glycol, and the like. In this case, water may be included in the polymerization mixture or post added after the polymerization is complete. In some cases, the polymer is prepared in a conventional organic solvent such as xylene, butyl acetate, methyl ethyl ketone, methyl tertiary butyl ether, and the like. When organic solvent is employed with or without water, it is convenient to use organic soluble-free radical initiators such as azo-bis-isobutyronitrile, t-butyl-peroctoate, or benzoyl peroxide and whatever heat is convenient to assure smooth copolymerization. Another route to preparation of a water-soluble polymer for this invention is to prepare a vinyl dispersion polymer having enough acrylic or methacrylic acid or other polymerizable acid monomer (usually greater than 10%) so that the emulsion polymer can be solubilized by addition of ammonia or other base. Water-soluble polymers of this type are advantageously used as blends with conventional dispersion polymers, preferably those which also have pendant acetoacetate functionality. The blend of alkali-soluble resin and latex polymer has a particularly advantageous property combination of gloss and rheology and is useful in coatings and printing ink applications.

In another embodiment of this invention, an aqueous dispersion contains copolymer particles made up of at least two mutually incompatible copolymers. These mutually incompatible copolymers may be present in the following morphological configurations, for example, core / shell, core / shell particles with shell phases incompletely encapsulating the core, core/shell particles with a multiplicity of cores, interpenetrating network particles, and the like. In all of these cases, the majority of the surface area of the particle will be occupied by at least one outer phase and the interior of the particle will be occupied by at least one inner phase. The mutual incompatibility of the two polymer compositions may be determined in various ways known in the art. The use of scanning electron microscopy using staining techniques to emphasize the difference between the appearance of the phases, for example, is such a technique.

The emulsion polymerization techniques used to prepare such dispersions are well known in the art. It is sometimes advantageous to introduce some crosslinking or gel structure by the sequential polymerization process in the core via low levels of a crosslinking monomer such as allyl methacrylate, diallylphthalate, diallyl maleate, butylene glycol dimethacrylate, divinyl benzene, triallyl isocyanurate, ethylene glycol diacrylate, and the like. The lightly crosslinked core does not adversely affect film formation and does in some cases result in better coatings, particularly when the pendant acetoacetate is concentrated in the shell.

As indicated above, a major use for this technology is for functionalizing vinyl polymers dispersed or dissolved in aqueous solvents. Unfortunately, vinyl polymers containing pendant acetoacetate are prone to hydrolysis in water, particularly on heat aging. The hydrolysis occurs at nearly any pH and yields acetoacetic acid, $$CH_3CCH_3 + CO_2$$

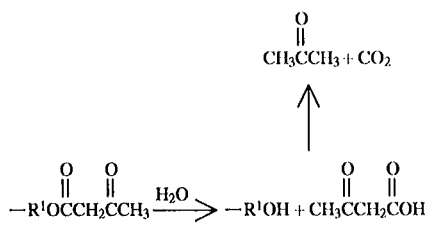

which in turn decomposes to acetone and carbon dioxide.

In an earlier application, U.S. Ser. No. 632,302, abandoned, the solution to this problem was provided by treating the aqueous acetoacetate polymer after preparation with one molar equivalent of ammonia or a primary amine such as ethanolamine, methyl amine, or isopropyl amine. As described in that application, typically, the polymer is neutralized to a basic pH with one of the aforementioned amines, preferably to a pH greater than 9. Under these conditions the enamine is formed. The reaction to form the enamine is generally rapid with the rate of formation increasing with temperature. In general, enamine formation is complete within 8 hours. An alternative approach is to raise the pH to about 9, allow the system to equilibrate, and readjust the pH to about 9 to replace the amine consumed by enamine formation. The enamine is stable to hydrolysis at pH's typically greater than 7.

We have now found that the enamine reaction route provides a method of attaching additional functional groups, or functionalized side chains to acetoacetate polymers. As shown in the following formula in which $R^2$ represents a functional group or a linking group which bears a functional group.

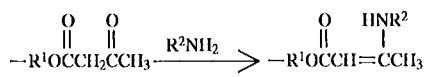

Sterically hindered primary amines such as t-butyl amine and aromatic amines such as aniline are generally less suitable because of incomplete enamine formation. The enamine formation is a reversible reaction so the amine compound should be non-volatile if the composition is likely to be exposed to the atmosphere prior to the application use of the functional group. The wet composition is quite storage stable, however, as long as it is stored under conditions (such as a closed container) where the volatile amine cannot evaporate.

Another approach to preparation of vinyl polymers containing equivalent pendant enamine functionality is to use preformed enamine monomers derived from the appropriate amine and the acetoacetate monomer. In this case, the pH must be kept on the alkaline side during polymerization to avoid hydrolysis of the enamine back to the acetoacetate.

Functional Groups

In the formula —$R^2NH_2$, $R^2$ can be a functional group, or a linking group bearing a functional group. Examples of linking groups are divalent groups such as $C_2$ to $C_{18}$ alkyl, alkoxyl and polyalkoxyl, such as polyoxyethylene and polyoxypropylene chains, having molecular weights of from about 72 to about 400,000.

Examples of types of property-imparting functional groups which may be attached through this method include crosslinking groups, adhesion promoters, ultraviolet blocking groups, surface active compounds, latex stabilizing groups, binding groups for separation, etc. Functional groups of this type are well known in the art such as, for example, mercaptoethyl amine, taurine, 3-aminopropyltrimethoxysilane, 3-aminopropyltriethyoxysilane, polyoxypropylencamine, polyoxyethylencamine, 2-aminoethylethylencurea, 2-dimethylaminoethylamine, amino acids, allylamine, 4-amino-2,2,6,6-tetramethylpiperidinyloxy-free radical, and the like.

In one embodiment, the compound bearing amine functionality and an additional functional group contains both primary amine functionality, for enamine formation, and a secondary or tertiary amine functionality. In the case of the tertiary amine, a route to a cationic latex is provided; when the tertiary amine functional polymer is treated with a proton source or alkylating agent, an ammonium cation can be produced.

A sterically stabilized latex can be produced for example through reaction of an acetoacetate polymer with a polyethoxylated amine. This technique also provides a route to control the polarity of the polymer by selecting from hydrophilic or hydrophobic amines. Similarly, the refractive index of the polymer can be adjusted using appropriate functional group on the amine to either raise or lower the refractive index. The compatibility of various pairs of polymers could also be improved for blending by adding selected functionalities on one or both polymers.

Monomers bearing certain functional groups are not generally suitable for incorporation into polymers, either due to the likelihood that the functionality would be chemically altered under the conditions of polymerization, or due to the tendency of the functional group to produce an undesired effect on the polymerization process. For example, a mercaptan functional group could cause a chain transfer effect during free radical polymerization, thus skewing the product profile toward lower molecular weight products than if a functionality that does not have a chain transfer effect were used. An olefinic functional group is likely to be consumed in a free radical polymerization process, but could be post-added according to the invention. A secondary amine can cause retardation and chain transfer during free radical polymerization.

Additives

The polymers and additives of this invention may be formulated for the chosen end use. Additives such as thickeners, dispersants, pigment, extenders, fillers, anti-freeze agents, plasticizers, adhesion promoters, coalescents, wetting agents, defoamers, colorants, non-aldehyde based biocides, soaps and slip agents may be incorporated.

The following examples are provided to illustrate some embodiments of the invention. They should not be read as limiting the scope of the invention which is more fully described in the specification and claims.

Unless otherwise indicated, percentages are by weight based on the total solids.

EXAMPLE 1

A polymer was prepared from a monomer mixture that contained 501.7 grams of water, 18.1 grams of Rhodapex CO-436 (an ammonium salt of sulfated nonylphenoxypoly (ethyleneoxy) ethanol; RhÔne Poulenc), 7.5 grams of methacrylic acid, 597.6 grams of acetoacetoxyethyl methacrylate, 888.9 grams of methyl methacrylate, and 44.9 grams of n-dodecyl mercaptan. From this monomer emulsion mixture, 47.2 grams was removed and added to a kettle containing a mixture of 1317.9 grams of water and 8.74 grams of Rhodapex CO-436 heated to 85° C. An initiator charge of 2.26 grams of sodium persulfate dissolved in 50.0 grams of water was added. Starting ten minutes later, the remaining monomer emulsion was gradually added over a two hour period along with 1.13 grams of sodium persulfate dissolved in 50 grams of water in a separate feed. After the two hour period, the emulsion was cooled to ambient temperature.

Solubilization of Polymer

To 500 grams of the emulsion which was reduced to 41.8% solids with water was added 370 grams (0.95 equivalents based acetoacetate functionality) of a 1000 molecular weight primary amine terminated polyethoxylate (Jeffamine M-1000, Texaco). The resulting mixture became a clear solution of a highly viscous material (Brookfield viscosity of 7160 cps) with solution like rheology.

This example illustrates that, with the appropriate amine, emulsion polymers can be solubilized to form uniform solution resins by enamine formation.

EXAMPLE 2

A polymer was prepared from a monomer mixture that contained 501.7 grams of water, 45.7 grams of a 23% solution of sodium dodecyl benzene sulfonate, 19.42 grams of methacrylic acid, 298.8 grams of acetoacetoxyethyl methacrylate, 578.2 grams of methyl methacrylate, 597.6 grams of butyl acrylate and 3.0 grams of n-dodecyl mercaptan. From this monomer emulsion mixture, 47.2 grams was removed and added to a kettle containing a mixture of 1317.9 grams of water and 22.0 grams of the sodium dodecyl benzene sulfonate solution heated to 85° C. An initiator charge of 2.26 grams of sodium persulfate dissolved in 50.0 grams of water was added. Starting ten minutes later, the remaining monomer emulsion was gradually added over a two hour period along with 1.13 grams of sodium persulfate dissolved in 50 grams of water in a separate feed. After the two hour period, the emulsion was cooled to ambient temperature. To aliquots of the emulsion was added 1 equivalent of the amine listed in Table A. The latex polymers were equilibrated for two days prior to freeze drying and the Tg of the polymer was determined by differential scanning calorimetry.

TABLE A

Effect of Formation of Enamines on the Tg of the Polymer

| Amine | Tg (°C.) |
| --- | --- |
| control (none) | 23 |
| ammonia | 26 |
| ethanolamine | 30 |
| 4-amine-2,2,6,6-tetramethylpiperidine | 39 |

This example illustrates that the Tg of the polymer can be adjusted after polymer formation by post addition of the selected primary amine and formation of the corresponding enamine.

EXAMPLE 3

Functional Monomer I (ethylethyleneureaenamine of allyl acetoacetate)

A functionalized monomer was prepared by treating allylacetoacetate (77 gm, 0.543 moles) with aminoethylethyleneurea (70 gm, 0.543 moles) in 149 grams of ethylacetate containing 0.4 grams of phenothiazine. The reaction mixture was heated to reflux while connected to a Dean-Stark trap (used to azeotropically remove water) for a total of 13 hours. The reaction solvent was then removed under reduced pressure using a rotoevaporator yielding a total of 122 grams of product:

EXAMPLE 4

Functional Monomer 2 (hydroxyethylenamine of AAEM)

A functionalized monomer was prepared by treating acetoacetoxyethylmethacrylate (AAEM) (200 gm) with ethanolamine (62.7 gm) in 500 gm of methylene chloride. The reaction mixture was stirred at room temperature for 20 minutes then heated to reflux for 1 hour then cooled to room temperature. The cooled reaction mixture was poured into a separatury funnel and washed twice with saturated sodium chloride solution. The organic solution was then dried using anhydrous potassium carbonate. The dried organic solution was filtered to remove the potassium carbonate. The resulting organic solution was then concentrated under reduced pressure using a rotoevaporator to yield 239 grams of the desired product: 1H NMR (270 MHz, CDCL3) d 1.85 (br s, 6H), 3.3 (br q, 2H), 3.62 (br t, 2H), 3.8 (m, 1H), 4.2 (m, 4H), 4.38 (s, 1H), 6.02 (s, 1H), 8.5 (m,1H).

EXAMPLE 5

Preparation of Solution Polymer Using an Enamine Functionalized Monomer

A reaction flask containing 286 grams of xylene was heated to 105° C. under a nitrogen atmosphere. A mixture of 120 grams of butylmethacrylate, 67 grams of butylacrylate, 10 grams of the enamine formed from, (AAEM and ethanolamine in Example 4), and 3 grams of methacrylic acid was feed to the reaction kettle concurrently with a mixture of 6 grams of t-butylperoctoate dissolved in 14 grams of xylene over a period of 2 hours. The reaction was then held at 105° C. for an additional 30 minutes at which time 0.5 grams of t-butylperoctoate was added to the reaction mixture. The reaction was held an additional 10 minutes at 105° C. then cooled to room temperature. The final solution was shown to contain 38% by weight solid polymeric material by drying a sample in an oven at elevated temperature (150° C. for 30 minutes). The polymer was shown to contain the enamine structure by taking a UV spectra of a thin film of the polymer cast on a quartz disk. The UV spectra contained a large absorption characteristic of betaaminocrotonates at a wavelength of 283 nm.

EXAMPLE 6

Vinyl Acetate Emulsion Polymer

An emulsion polymer of overall composition 96.45 vinyl acetate/3.3 allylacetoacetate/0.25 sodium vinylsulfonate was prepared by adding a monomer mixture that contained 490 grams of water, 1.8 grams of a 58% solution of the ammonium salt of nonylphenoxypolyethylenoxidesulfonate (Rhodapex CO-436), 3 grams of acetic acid, 3.6 grams of sodium acetate, 2083.4 grams of vinyl acetate, 21.6 grams of sodium vinylsulfonate, and 71.3 grams of allyl acetoacetate to a reaction kettle containing 1026 grams of water (heated to 60° C.), 60 grams of a 45% solution containing 100 nm particles of a BA/MMA/MAA latex polymer, 24 grams of a 2.75% aqueous solution of sodium persulfate, 24 grams of a 1.25% aqueous solution of sodium bisulfite,. 12.0 grams of a 0.2% aqueous solution of ferrous sulfate, 3 grams of acetic acid, and 3 grams of sodium acetate. The above monomer emulsion was fed into the reaction kettle concurrently with a solution of 120 grams of 2.25% sodium bisulfite and a solution of 2.4 grams of t-butylhydroperoxide, 1.8 grams of sodium persulfate, and 120 grams of water over a period of 3.5 hours under a nitrogen atmosphere. Following the addition of monomer, the reaction was maintained at 60° C. for 15 minutes then a solution of 30 grams of 8% aqueous t-butylhydroperoxide was added to the kettle along with a solution of 120 grams of 5% aqueous isoascorbic acid. The reaction was then cooled to room temperature to yield a latex containing 51.6% solids polymer.

EXAMPLE 7

Functionalization of a Vinyl Acetate Emulsion

A sample of 100 grams of emulsion polymer from Example 6 was treated with 1.55 grams of aminoethylethyleneurea. The reaction was held at room temperature. The next morning, a thin film of the polymer on a quartz disk was shown to contain the UV absorption peak characteristic of the beta-aminocrotonate structure at a wavelength of 280 nm).

EXAMPLE 8

(Meth)acrylate Emulsion Polymer

A polymer was prepared from a monomer mixture that contained 629.99 grams of water, 9.89 grams of a 23% aqueous solution of sodium dodecylbenzene sulfonate, 790.02 grams of butyl acrylate, 686.57 grams of methyl methacrylate, 376.20 grams of acetoacetoxyethylmethacrylate, and 28.22 grams of methacrylic acid. From this monomer emulsion, 58.72 grams was removed and added to a reaction kettle heated to 85° C. containing 1577.93 grams of water, 8.22 grams of a 23% aqueous solution of sodium dodecylbenzene sulfonate, 3.02 grams of sodium persulfate. The monomer emulsion was added to the kettle concurrently with 50 grams of a 1.7% aqueous solution of sodium persulfate over 180 minutes. Following the additions, the reaction was held at 85° C. for 30 minutes then cooled to 65° C. When the reaction mixture reaches 65° C. 1.0 grams of a 0.48 aqueous solution of ferrous sulfate, 0.54 grams of 70% active t-butylhydroperoxide dissolved in 19 grams of water, and 0.38 grams of isoascorbic acid dissolved in 19 grams of water are added to the reaction kettle. The reaction is held at 65° C. for 15 minutes and the reaction cooled to room temperature. this produced an emulsion polymer at 43.3 % solids.

EXAMPLE 9

Preparation of a Cationic Latex

A 10 gram sample of experimental latex prepared in Example 8 was diluted with 33.3 grams of 0.1 molar potassium chloride and 0.18 grams of Triton X-405 (a 70% aqueous solution, from Union Carbide). This latex sample was then treated with 0.356 grams of dimethylaminoethylamine and equilibrated overnight. The acoustophoretic mobility was measured while varying the pH of the system using a Penkem 7000 instrument. The relative acoustophoretic mobility (RAM) was approximately $-1.8 \cdot 10^{-10}$ from pH 10 to 8.5, from pH 8 to 2 the RAM was $+1.2 \times 10{-10}$. This clearly demonstrates that the latex is anionic (negatively charged) at high pHs and cationic (positively charged) at low pHs, where the tertiary amine group is either uncharged or protonated respectively, and therefore the tertiary amine group must be attached to the latex particles.

EXAMPLE 10

Latex polymer A is a two stage emulsion polymer of composition 50 (54 2-ethylhexyl acrylate/2.0 styrene/25 acrylonitrile/4 methacrylic acid/15 acetoacetoxyethylacrylate)//50 (40 isobutylmethacrylate/58 methylmethacrylate/2 methacrylic acid) at 39.7% solids. Latex B is a two stage emulsion polymer of composition 50 (3 butylacrylate/91.6 styrene/4.4 divinylbenzene/1 methacrylic acid)//50 (83 butylacrylate/10 acetoacetoxyethylacrylate/7 methacrylic acid) at 41.6% solids, both of which are prepared via conventional techniques well known in the art. The below listed examples are prepared by taking a sample of latex (100 gm) and treating it with butyl cellosolve (8.93 gm) and butyl Carbitol (2.98 grams) then adding the appropriate amount of the listed functional amine.

| Amine | Amount | Latex | MEK Swell Ratio | Acetone Spot Test | Print Resistance |
| --- | --- | --- | --- | --- | --- |
| none (control) | 0 | A | 7.3 | 1 | 3 |
| 2-(2-aminoethyl)-aminoethanol | 1.45 | A | 4.5 | 5 | 7 |
| 4-amino-2,2,6,6-tetramethyl-piperidine | 2.17 | A | 5.1 | N/A | 9 |
| none (control) | 0 | B | 4.5 | 0 | 4 |
| 2-(2-aminoethyl)-aminoethanol | 1.01 | B | 3.8 | 4 | 7 |
| N-methyl ethylenediamine | 1.13 | B | 3.3 | 9 | 5 |
| 2-((3-aminopropyl amino)-propanel | 0.86 | B | 3.4 | 6 | 7 |

| Amine | Amount | Latex | MEK Swell Ratio | Acetone Spot Test | Print Resistance |
|---|---|---|---|---|---|
| N-ethyl ethylenediamine | 0.72 | B | 3.3 | 6 | 4 |

The above examples demonstrate that the use of diamines (where one amine is a primary amine and the other amine is a secondary amine) can improve the solvent resistance and print resistance of clear coatings for use on wood, as well as other solid substrates.

TEST METHODS

Print Resistance Test

A film is cast 1 mil DFT on aluminum and air dried for 4 hrs. A piece of cheesecloth is placed on the film and a weight is placed on the cheesecloth to give a pressure of 4 psi. After 4 hrs., the weight and cheesecloth are removed and the film is examined for any impression made by the cheesecloth. The samples are rated on a 0 to 10 scale, where 0 represents complete failure, with the cheesecloth irreversibly adhered to the coating, and a 10 being no visual damage to the coating when the cheesecloth is removed.

Acetone Spot Test

A film is cast 1 mil DFT on aluminum and air dried for I week. A glass fiber filter disk (Gelman 66075 or equiv.) is soaked in acetone and then placed on the film and covered with a watch glass. After 2 minutes, the filter is removed, the excess acetone is blotted off with a tissue, and the film is examined for any damage. The samples are rated on a 0 to 10 scale, where a 0 represents a complete failure with the coating dissolving in the solvent and a 10 representing a coating having no visual damage.

MEK Swell Ratio Test

A film of the latex polymer, approximately 10 to 12 mils thickness wet leading to a dry film thickness of approximately 2 mils dry, is cast onto a sheet of polypropylene. The dry film is removed from the polypropylene and cut into a 1 cm by 1 cm square sample. The sample is soaked in methylethylketone for 2 hours. The swollen sample is removed from the solvent and the length of one edge is measured. The resulting length is then cubed to give the reported swell value. A lower value represents inherently better solvent resistance of the coating.

GLOSSARY

When used in this application, the abbreviations shown in the following list have the meanings indicated:

The $T_g$ of a polymer is a measure of the hardness and melt flow of the polymer. The higher the $T_g$, the less the melt flow and the harder the coating. $T_g$ is described in *Principles of Polymer Chemistry* (1953), Cornell University Press. The $T_g$ can be actually measured or it can be calculated as described by Fox in *Bull. Amer. Physics Soc.*, 1,3, page 123 (1956). $T_g$, as used herein, refers to actually measured values. For measurements of the $T_g$ of a polymer, differential scanning calorimeter (DSC) can be used (a rate of heating of 10 degrees centigrade per minute, with $T_g$ taken at the first inflection point).

DFT is the Dry Film Thickness.

We claim:

1. A process for producing storage stable functional polymers comprising reacting an aqueous acetoacetate-functional polymer with a compound which has primary amine and at least one other type of functional group at conditions which favor formation of the enamine and storing the resulting liquid aqueous composition.

2. A process for preparing an aqueous polymer having functional groups comprising polymerizing a monomer mixture which contains acetoacetate monomer at conditions which are incompatible with a functional group and then after polymerization, reacting the acetoacetate-functional polymer product with a compound which has primary amine and the incompatible functional group at conditions which favor formation of the enamine.

3. The process of claims 1 or 2 wherein the amount of functional amine can be varied over a range of from about 0.1 equivalence to about 1.5 equivalence of amine, based on the amount of acetoacetate functional group.

4. The process of claims 1 or 2 wherein the $T_g$ of the polymer is modified by the addition of functional amines.

5. The process of claim 2 wherein the polymerization is a free radical polymerization and the incompatible functional group is selected from the group consisting of mercaptan, olefinic and secondary amine functional groups.

* * * * *